(12) United States Patent
Lee

(10) Patent No.: US 8,048,116 B2
(45) Date of Patent: *Nov. 1, 2011

(54) FACET JOINT PROSTHESIS

(75) Inventor: Casey K. Lee, Florham Park, NJ (US)

(73) Assignee: Re-Spine LLC, Florham Park, NJ (US)

( * ) Notice: Subject to any disclaimer, the term of this patent is extended or adjusted under 35 U.S.C. 154(b) by 60 days.

This patent is subject to a terminal disclaimer.

(21) Appl. No.: 12/463,008

(22) Filed: May 8, 2009

(65) Prior Publication Data

US 2009/0216275 A1    Aug. 27, 2009

Related U.S. Application Data

(63) Continuation of application No. 10/893,243, filed on Jul. 19, 2004, now Pat. No. 7,537,611.

(60) Provisional application No. 60/487,604, filed on Jul. 17, 2003.

(51) Int. Cl.
*A61B 17/70* (2006.01)
*A61B 17/88* (2006.01)

(52) U.S. Cl. ....................... 606/247; 606/279

(58) Field of Classification Search ............... 606/246, 606/60, 247, 248, 70, 71, 250, 252, 279; 623/17.11–17.16
See application file for complete search history.

(56) References Cited

U.S. PATENT DOCUMENTS

| | | | |
|---|---|---|---|
| 5,571,191 A | 11/1996 | Fitz | |
| RE36,758 E * | 6/2000 | Fitz | 623/17.11 |
| 6,132,464 A | 10/2000 | Martin | |
| 6,419,703 B1 | 7/2002 | Fallin et al. | |
| 6,610,091 B1 * | 8/2003 | Reiley | 623/17.11 |
| 6,902,580 B2 * | 6/2005 | Fallin et al. | 623/17.11 |
| 6,949,123 B2 * | 9/2005 | Reiley | 623/17.11 |
| 7,087,084 B2 * | 8/2006 | Reiley | 623/17.11 |
| 7,147,664 B2 | 12/2006 | Louis et al. | |
| 7,537,611 B2 * | 5/2009 | Lee | 623/17.11 |

FOREIGN PATENT DOCUMENTS

| | | |
|---|---|---|
| WO | 01/30248 | 5/2001 |
| WO | 03/041618 | 5/2003 |

OTHER PUBLICATIONS

Yang et al., "Mechanism of Facet Load Transmission as a Hypothesis for Low-Back Pain", SPINE, vol. 9, No. 6, Dec. 31, 1983, pp. 557-565.
El-Bohy et al., "Experimental Verification of Facet Load Transmission by Direct Measurement of Facet Lamina Contact Pressure" *J Biomechanics*, vol. 22, No. 8/9, Aug. 2, 1989, pp. 931-941.
Farfan et al., "The Effects of Torsion on the Lumbar Intervertebral Joints: The Role of Torsion in the Production of Disc Degeneration", *The Journal of Bone and Joint Surgery*, vol. 52, No. 3, Apr. 1970, pp. 468-497.

* cited by examiner

*Primary Examiner* — Pedro Philogene
(74) *Attorney, Agent, or Firm* — Miles & Stockbrigde P.C.

(57) ABSTRACT

A prosthetic implant for replacing a facet joint of a spinal motion segment includes a generally conical superior component adapted to be implanted at a surgically prepared site on a lower articular process of a cephalad vertebra of a spinal motion segment, and a cup-shaped inferior component adapted to be implanted at a surgically prepared site on a superior articular process of a caudad vertebra of the spinal motion segment.

22 Claims, 14 Drawing Sheets

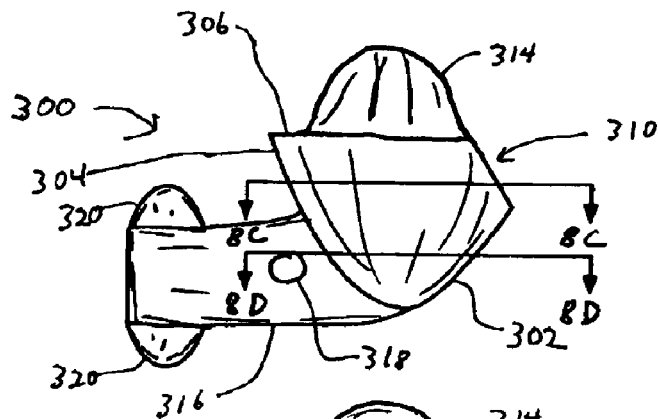
Fig. 8A
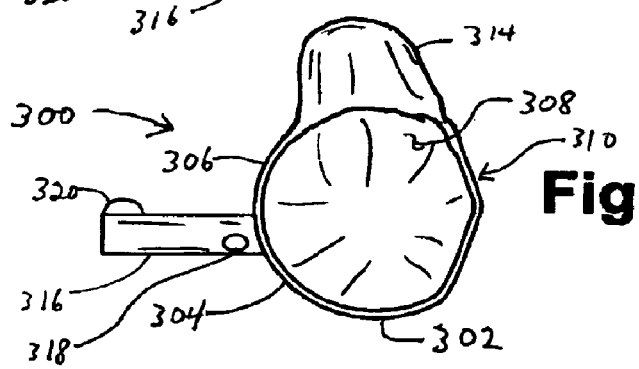
Fig. 8B
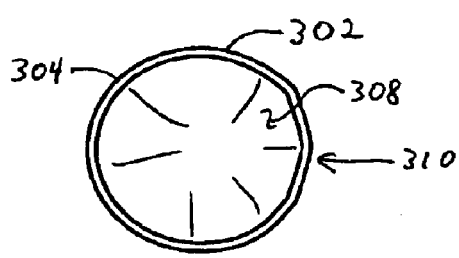
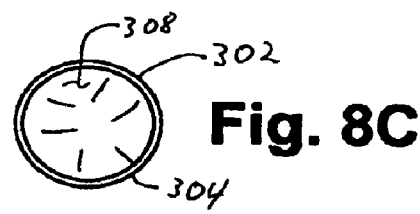
Fig. 8C
Fig. 8D
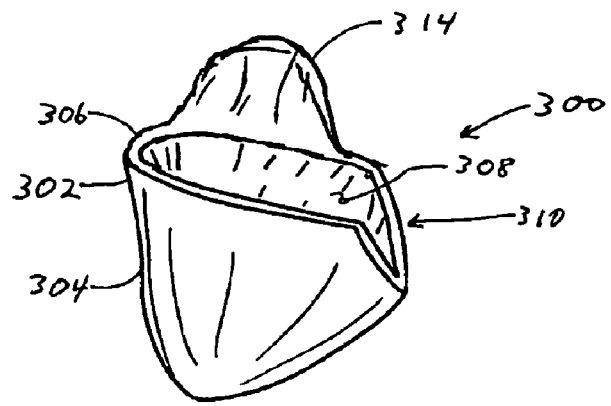
Fig. 8E

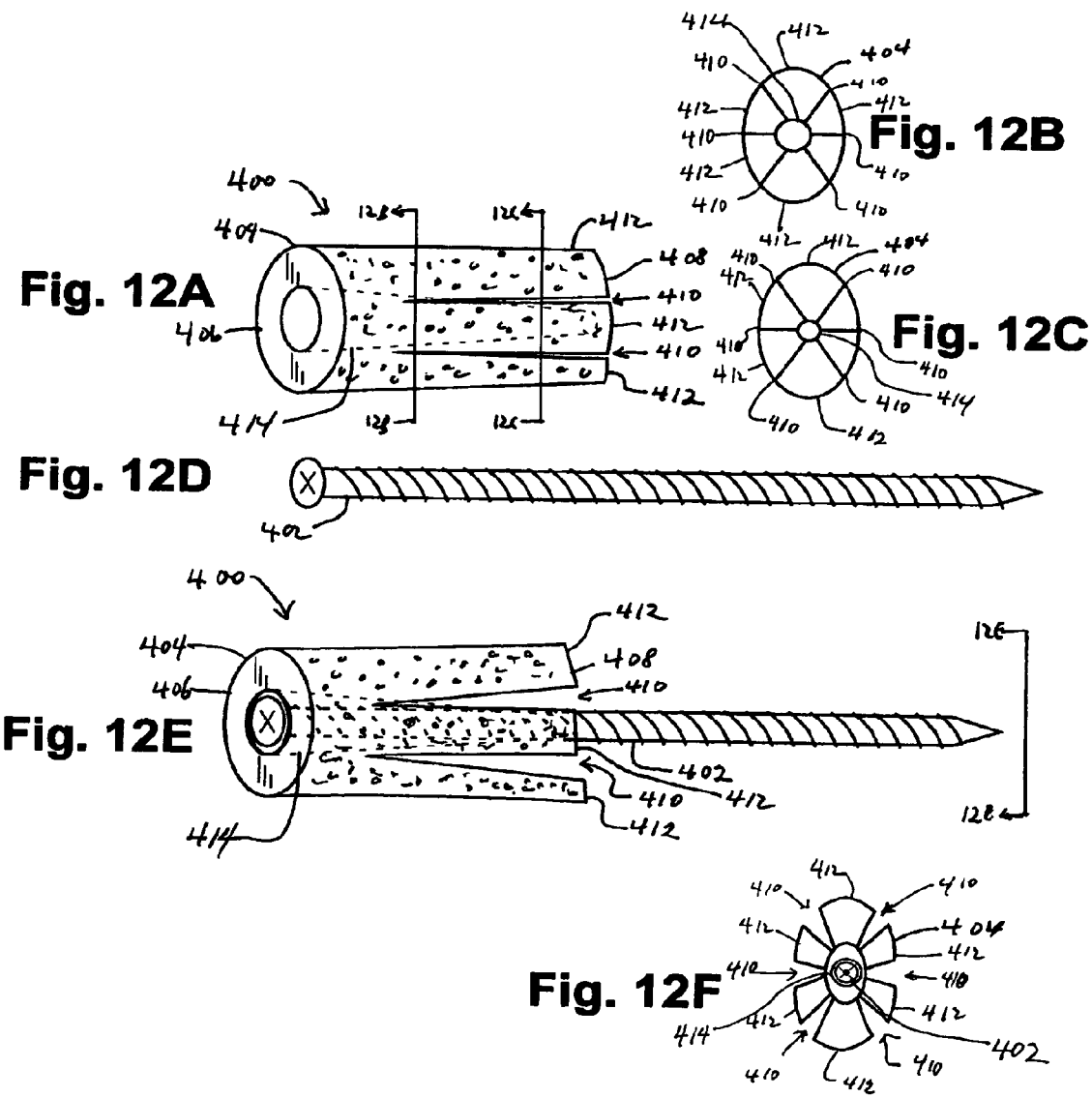

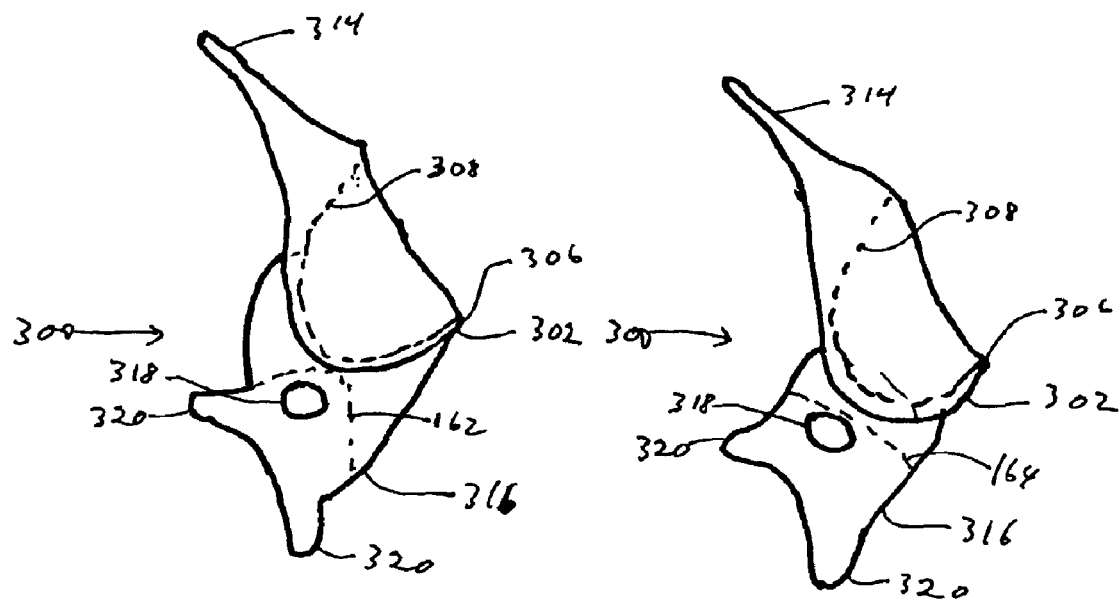
Fig. 14A  Fig. 14B
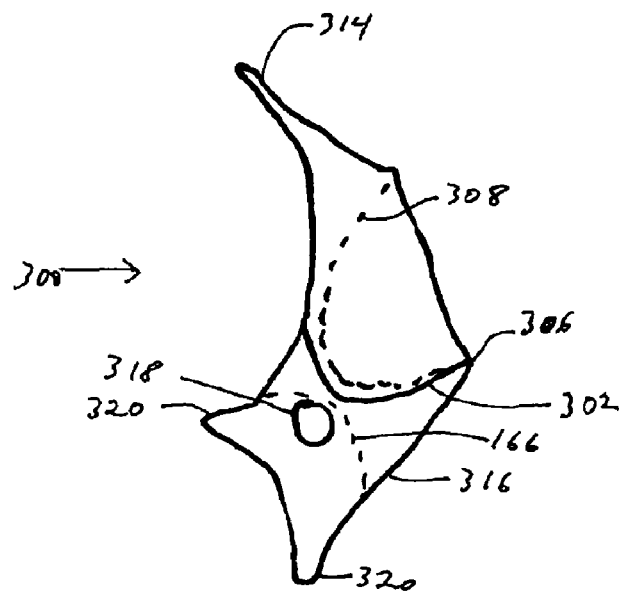
Fig. 14C

FACET JOINT PROSTHESIS

CROSS-REFERENCE TO RELATED APPLICATION

This application is a continuation of application Ser. No. 10/893,243 filed Jul. 19, 2004 now U.S. Pat. No. 7,537,611. This application also claims the benefit of the priority of U.S. Provisional Patent Application No. 60/487,604, filed Jul. 17, 2003, the entire disclosure of which is incorporated herein by reference.

BACKGROUND OF THE INVENTION

1. Field of the Invention

This invention relates to prostheses for replacing structures of the human spine and more particularly to prostheses for replacing a facet joint.

2. Brief Description of the Prior Art

Lower back pain is a very common disorder and is responsible for extensive morbidity and lost time at work. The prevalence rate of low back pain is very high, affecting approximately 80% of the general population at some time. Although most patients experience the painful symptoms only occasionally and recover fully, approximately 10% of these patients experience chronic and disabling low back pain in spite of various medical treatments.

The most common cause of chronic disabling low back pain is degenerative disk disease (DDD). Another problem associated with low back pain, which often accompanies DDD is degeneration of the facet joints between vertebrae.

Anatomy and Biomechanics of the Facet Joints:

The functional unit of the spinal column is a spinal motion segment that is made of a three-joint complex, a disc and two facet joints. The facet joint is a synovial joint with the joint surfaces covered by hyaline cartilage like other diarthrodial joints. The orientation of the facet joints in the lumbosacral spine is symmetrical on both sides in almost all individuals, but it is occasionally found to be asymmetrical. Facet asymmetry has been reported in the literature to cause disc degeneration. The facet joint is generally oriented obliquely in sagittal and coronal planes. The orientation of the facet joints is significantly different at different levels within the spine, i.e., the cervical, thoracic, thoraco-lumbar, and lumbo-sacral regions of the spine. Within the lumbar or lumbo-sacral spine the size, shape, orientation, and angle of the facet joints have a wide range of variation among the motion segment ins different levels within an individual. Such variations are even greater among different individuals.

Although the disc is the principal structure performing the functions of weight bearing, stabilization, and motion in a spinal motion segment, the facet joints also contribute significantly to these functions.

Weight bearing function: The facet joints are responsible for approximately 20% of the weight bearing function of a spinal motion segment at the neutral erect posture. The weight bearing function of facet joints decreases on flexed posture and increases on extension (up to 40%). Biomechanical studies have shown that the facet joint capsule primarily takes up the weight bearing function of the facet joints in the axial direction. Such studies include: Al-Bohy A A, Yang K H, King A I: Experimental verification of facet load transmission by direct measurement of facet lamina contact pressure. J Biomech. 22: 931-941, 1989, and Yang K H, King A I: Mechanism of facet load transmission as a hypothesis for low back pain. Spine 9: 557-565, 1984.

Motion: The facet joints, two opposing articular processes, glide during flexion-extension, rotate during torsion, and toggle during lateral bending of the spinal motion segment. The motion at the facet joints is not a mere passive motion, but a positively guided motion by the shape, orientation, and angle of the facets and by the joint capsule. In a normal spinal motion segment, the facet joints become "locked" during extension, thus allowing less rotational and gliding motion to promote weight-bearing stability. In flexion, the facet joints are less engaged, which allows for freer motion.

Stability of a spinal motion segment: The disc is the principal stabilizer for an intact spinal motion segment. However, the facet joints are important stabilizing structures for torsion and shear stability in the spinal motion segment. The facet joints are responsible for approximately 45-50% of the torsional stability, and the disc is responsible for approximately 50-55% of the torsional stability. Torsional stability of the spinal motion segment is discussed in: Farfan H F, Cossette J W, Robertson G H, et al: The effects of torsion on the lumbar intervertebral joints: The role of torsion in the production of disc degeneration. J Bone and Joint Surg. 52A: 468-497, 1970. When the disc degenerates and loses its stabilizing function, the facet joints become an even more important stabilizer. Facet joints are important structures for protecting the disc by limiting excessive torsional and shear motion.

Structural changes of the facet joint are usually seen in the late stage of degeneration of a spinal motion segment. Isolated facet joint degeneration in the absence of disc degeneration is very rare. The pathology of the degenerated facet joint is very similar to that observed in other weight bearing synovial joints, and includes synovial and capsular hypertrophy, joint effusion/cyst, bony hypertrophy, and/or joint subluxation. Hypertrophy of the facet joint capsule, synovium or bone may cause spinal stenosis. Decompression with or without spinal fusion is sometimes indicated for patients with chronic disabling low back pain or stenotic symptoms caused by severe degenerative changes of the facet joints that are not responding to non-operative treatments.

Decompression for spinal stenosis provides successful relief of symptoms, but the recurrence rate of symptoms is very high (40-50% in 5 years). Spinal fusion often provides good results but has adverse effects. Novel ideas of replacement of a painful and dysfunctional disc with an artificial disc prosthesis have been evolved recently. Some disc prosthesis designs have been used clinically in recent years. The artificial disc prosthesis is best indicated for patients with painful DDD with no or little facet joint degeneration. In advanced degenerative changes of a spinal motion segment, all three joints (the disc and facet joints) are affected, and replacement of the disc alone will not provide satisfactory results. Replacement of all three joints (a disc and two facet joints) may be required for satisfactory results with restoration of the motion segment function.

The requirements for a successful artificial facet joints prosthesis are: 1) It should provide an adequate range of motion for flexion-extension glide, rotation, and toggle during lateral bending of the disc. 2) It should provide stability, especially for torsional and shear motion. 3) It should provide a weight-bearing function of 20-30% of the physiological load. 4) The prosthetic components should have adequate fixation to the bone to overcome a very repetitive and a high bending moment and shear forces especially on the superior articular process. 5) It should provide a positive guidance of motion, especially for rotation and for flexion and extension. 6) It should be user-friendly, by overcoming the problem of a wide range of variability of size, shape, angle, and orientation. A prosthesis that lacks any one of these features will be prone to malfunction or become loose and thereby place untoward stress on the disc and the adjacent levels.

A number of attempts have been made to provide a satisfactory prosthesis for replacing the human facet joints.

U.S. Pat. No. 5,571,191, (and Reissue Pat. No. RE36,758) to William R. Fitz, entitled "Artificial Facet Joint" discloses a prosthesis having a superior component of conical or pyramidal shape that is fixed to the distal portion of the inferior articular process, e.g., with a bone screw or the like. The inferior component of the prosthesis is also roughly conical or pyramidal with one side somewhat elongated posteriorly and medially. It is distally fastened to the superior articular process. This prosthesis functions primarily as a surface interposition on the facet joints by capping the inferior and superior articular processes without altering the bony anatomy. The caps are fixed to the underlying bony articular processes by screws, and may have a porous coating on their interior surfaces to promote ingrowth of bone.

However, because of the very wide variation among individual patients in angle, orientation, size, and shape of the facets, a single set of conical or pyramidal caps will not be capable of matching all bone structures found in various individuals. In order to match all the naturally occurring variations, an almost unlimited number of sets of caps having different sizes, shapes, angles and orientations would be required. Another problem that may be encountered with this design is related to the stability of the implanted prosthetic device. Simple fixation of the caps to the underlying articular processes may not withstand repetitive torsional, bending and shear forces. The generally conical internal shape of the superior component may allow motion at the interface between the bone of the inferior articular process and the prosthesis. Furthermore, the inferior component, fastened to the superior articular process, may also not withstand a very high bending moment and shear force. Finally, the articulating surfaces between the inferior and superior components may not provide stability during torsional motion, especially during compression-torsion motion. Also this prosthesis may have difficulty in providing a substantial weight bearing function in the axial direction.

U.S. Patent application No. 2002/0123806 to Mark A. Reiley, (now U.S. Pat. No. 6,610,091) entitled "Facet Arthroplasty Devices and Methods", discloses a universal facet prosthesis having a concentric ball (inferior facet) and saucer or shallow socket (superior facet). It is designed for replacement of the lamina, superior articular processes and inferior articular processes after resection of those structures, unilaterally or bilaterally. The parts of the prosthesis are fixed into the vertebral bone through the pedicle with a screw or a peg. Alternatively, they may be fixed to the spinous process. Unilateral or bilateral variations are disclosed.

In this design, the concentric ball and shallow socket (or saucer) may have difficulty in meeting the above requirements, especially the requirement to provide positive torsional stability and shear stability during flexion of the motion segment. The inability of the vertebral motion segment structure to control the torsion during compression-flexion was found, in a biomechanical study by Farfan, (Farfan H F, Cossette J W, Robertson G H, et al: The effects of torsion on the lumbar intervertebral joints: The role of torsion in the production of disc degeneration, *J. Bone and Joint Surg.* 52A: 468-497, 1970), to be the most significant cause of injury to the disk. In the normal spinal motion segment, the rotary motion has its center near the posterior vertebral body (in front of the facet joints), and is accompanied by lateral-medial displacement of the inferior facets with respect to the superior facets on both sides. However, a concentric ball and socket or saucer design will be expected to have difficulty in reproducing the natural action of the facet joints during spinal rotation. Furthermore, single-point fixation into the vertebral body through the pedicle may not provide satisfactory fixation of the device so that it is capable of withstanding the repetitive stress involving the large bending moment and shear force acting upon the superior articular prosthesis during compression-flexion and compression-torsion.

U.S. Pat. No. 6,132,464, to Jean-Raymond Martin, entitled "Vertebral Joint Facets Prosthesis" discloses a prosthesis comprising two synthetic sliding surfaces in contact, one for the superior face and one for the inferior facet. The underlying bony structures are undisturbed, and these sliding surfaces cover the superior and inferior facets. The device is fixed in position by screw fixation into the pedicle, or by other means such as hooks, claws, or a clamping collar around the transverse process, or by a support plate or fixation to the spinous process.

However, because of the wide natural variation in the anatomy of the facet joints, it is expected to be difficult to provide a proper fitting or contouring of the prosthesis to the underlying bony structure. Because of the great anatomical variation among individuals, and the variation among the different motion segments within an individual, it may require a great many different prostheses having varied sizes, shapes, and orientations. Furthermore, in this prosthesis, the structure that connects the two sliding surfaces of the facets is located anterior-lateral to the pars interarticularis of the lamina. However, the exiting dorsal nerve root and the post-ganglion nerve also pass through this region. Consequently, crowding of the neural structures may be a problem.

U.S. Pat. No. 6,132,464, to T. Wade Fallin, entitled "Prosthesis for replacement of a Posterior Element of a Vertebra", discloses a prosthesis designed to replace all of the posterior spinal structures after resection of the spinous process, bilateral facet joints, and lamina. The basic unit comprises a prosthetic lamina with concave/convex-shaped "blades" for articular facets. Alternate embodiments include structure, in addition to the basic unit, to replace the spinous process, transverse processes, and/or the pedicle. Fixation of the device is accomplished by screws fixed in the pedicles.

However, because the natural facets are replaced by convex/concave sliding blades, the device may lack positive motion guidance or stability. Furthermore, a question may be raised as to whether fixation to the pedicles provides a sufficiently secure fixation for a permanent prosthesis.

In summary, certain problems are apparent in most of the previous designs for facet joint prostheses.

1) The contact surface area, the quantity and direction of force transmitted from the inferior articular process of the cephalad vertebra to the superior articular process of the caudad vertebra changes constantly during the normal range of motion of a spinal motion segment. Any prosthetic device that has fixed-angle contact surface areas, such as a ball-and-socket or ball-and-saucer joint may not be able to provide a wide variable arc of motion, stability and weight-bearing function.

2) The facet joint is a very important joint for providing stability against anterior shear during flexion, when the bending moment acting on the superior articular facet is relatively large. Permanent fixation of the prosthetic superior articular process or surface to the underlying bone is critical. The bony mass of the superior articular process is too small for adequate mechanical fixation by screws, pins, or pegs, or by capping to withstand such a very large bending moment (½ of the body weight×8-16 inches bending moment during flexion).

3) A prosthesis device for the inferior articular process that is fixed thereto through a structure having a substantially circular or oval cross-section may well be prone to loosen under the stress of rotational force.

Accordingly, a need has continued to exist for a facet joint prosthesis that is not subject to the deficiencies of the hitherto available prostheses.

SUMMARY OF THE INVENTION

The problems of the known facet joint prostheses have been alleviated by the facet joint prosthesis of this invention.

A prosthetic implant for replacing a facet joint of a spinal motion segment includes:
- a superior component adapted to be implanted at a surgically prepared site on a lower articular process of a cephalad vertebra of a spinal motion segment, wherein the superior component comprises a generally conical article having a smooth generally conical external surface and a tapered internal cavity adapted to be implanted on a tapered resected portion of said inferior articular process of said cephalad vertebra, and
- an inferior component adapted to be implanted at a surgically prepared site on a superior articular process of a caudad vertebra of the spinal motion segment, wherein the inferior component comprises a cup adapted to receive the conical external surface of the superior component and a base adapted to be implanted at the surgically prepared site on the superior articular process.

The superior component is a generally conical element adapted to fit over the surgically resected distal end of the inferior articular process of the cephalad vertebra. The conical superior prosthesis is adapted to be received in a cup-shaped lower element implanted in a surgical site formed at the general location of the superior articular process of the caudad vertebra.

Accordingly, it is an object of the invention to provide a prosthesis for replacing a facet joint in a spinal motion segment of the human vertebral column.

A further object is to provide a conical prosthesis for implantation on a surgically prepared distal end of an inferior articular process of a cephalad vertebra of a spinal motion segment.

A further object is to provide a cup-shaped prosthesis for implantation on a caudad vertebra of a spinal motion segment to receive the conical superior prosthetic element.

A further object is to provide a generally conical prosthesis having an internal cavity of generally triangular cross-section for implantation on a surgically prepared distal end of an inferior articular process of a cephalad vertebra of a spinal motion segment.

Additional objects of the invention will be apparent from the description of the invention which follows.

BRIEF DESCRIPTION OF THE DRAWINGS

FIG. 8A is a dorsal elevational view of the superior articular process prosthesis.

FIG. 8B is a plan view of the superior articular process prosthesis.

FIGS. 8C and 8D are cross-sectional views of the superior articular process along the lines indicated as 8C-8C and 8D-8D, respectively, in FIG. 8B.

FIG. 8E is a perspective view of the cup element of the superior articular process prosthesis.

FIG. 12A shows an expandable sleeve element of a fastener for fixing the inferior cup-shaped element of the prosthesis of the invention to the caudad vertebra of a spinal motion segment.

FIG. 12B shows a cross-sectional view of the expandable sleeve of FIG. 12A in the direction indicated as 12B in FIG. 12A FIG. 12C shows a cross-sectional view of the expandable sleeve of FIG. 12A in the direction indicated as 12C in FIG. 12A FIG. 12D shows a pedicle screw suitable for use with the expandable sleeve of FIG. 12A.

FIG. 12E shows the assembled sleeve and pedicle screw of FIGS. 12A and 12D.

FIG. 12F shows an end view of the assembly of FIG. 12D in the direction indicated as 12E in FIG. 12D, showing the expanded shroud.

FIGS. 14A, 14B, and 14C illustrate different embodiments of the cup-shaped inferior element of the prosthesis appropriate for different amounts of resection of the superior articular process.

DETAILED DESCRIPTION OF THE INVENTION AND PREFERRED EMBODIMENTS

Figure 1:
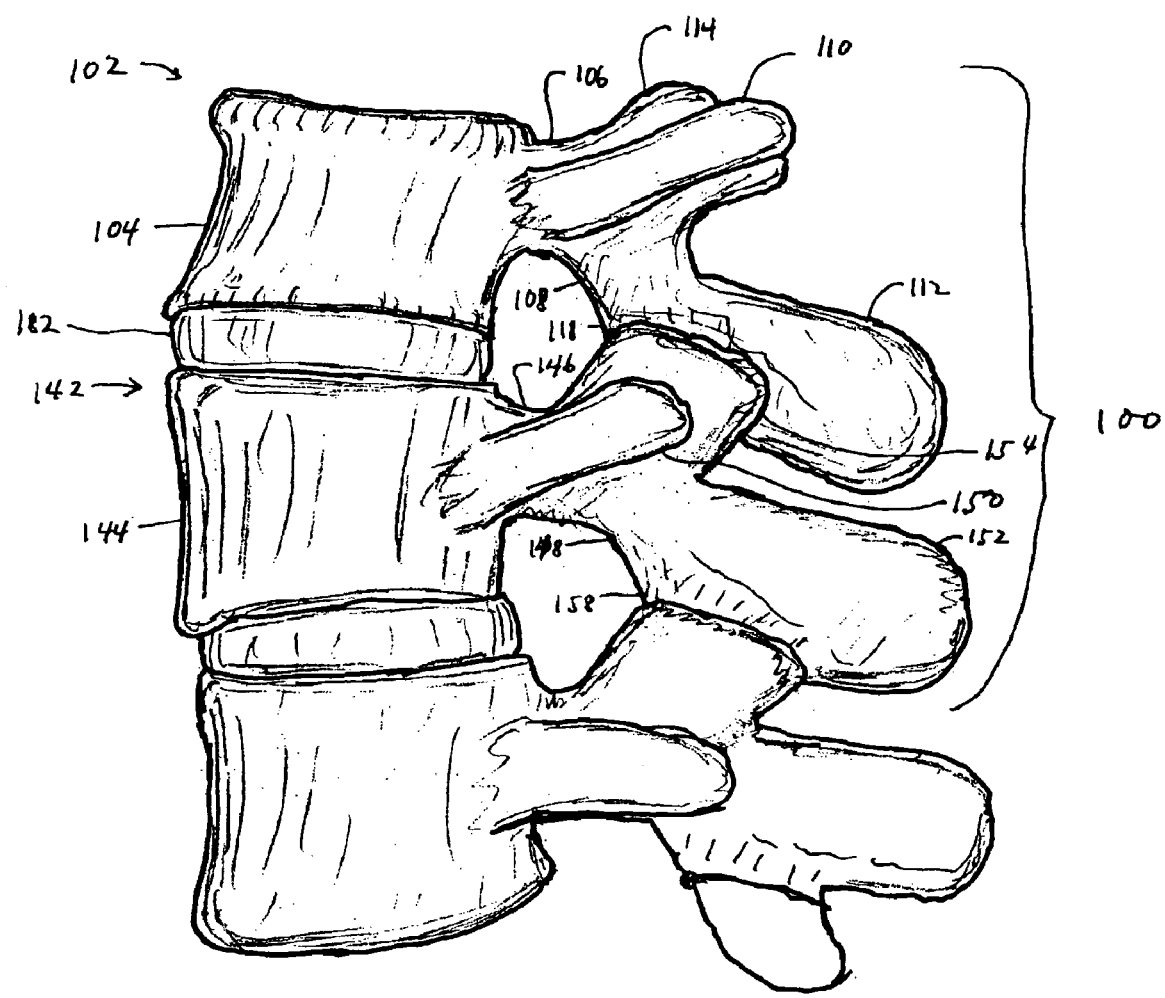
FIG. 1 is a lateral view of the lumbar vertebral column showing the spinal motion segment.

The design of the improved facet joint prosthesis of the invention is intended to overcome the disadvantages of the previous designs.

The improved facet joint prosthesis of the invention comprises two articulating elements:
a) a generally conical prosthesis for the inferior articular process of the cephalad vertebra, and b) a generally cup-shaped prosthesis for the superior articular process of the caudad vertebra that receives the conical prosthesis of the cephalad vertebra.

The articulating elements of the prosthesis are fixed to their respective vertebrae with appropriate fixation devices. These fixation devices may be of the types conventionally used in spinal prosthesis fixation. Alternatively, one or more of the fixation devices may have a preferred structure as discussed below.

The conical prosthesis for the cephalad vertebra ("the cone") has a generally circular cross-section. An interior cavity extending from the base of the cone into the interior of the cone receives the resected distal end of the inferior articular process of the cephalad vertebra. Preferably the interior cavity of the cone is provided with a porous surface to promote bone ingrowth as is conventional in bone implants. In order to resist rotational forces on the cone, the interior cavity is preferably given a cross-section that is other than circular, e.g., polygonal or elliptical, and the distal end of the inferior articular process is given a complementary cross-sectional shape. Inasmuch as the inferior articular process has a natural cross-section that is roughly triangular, it is preferred that the cone element of the prosthesis have an internal cavity that is generally triangular in cross-section in order to fit securely on the inferior articular process. The cone may also be provided with an internal axial projection extending from the apical region of the internal cavity to fit into a corresponding hole drilled in the end of the inferior articular process.

The external surface of the cone is smooth for gliding articulation with the cup prosthesis implanted at the location of the superior articular process of the caudad vertebra.

Fixation of the cone to the inferior articular process may be accomplished by a number of features. The hollow internal cavity of the cone is sized and shaped to fit the end of the resected inferior articular process, and may have an internal projection from the apex of the cavity to fit into a prepared channel in the inferior articular process. The interior cavity is preferably triangular in cross-section to provide a firm fit on the resected process, as indicated above, and is preferably provided with a porous coating for bone ingrowth. The prosthesis may also be fixed to the articular process with conventional bone cement or chemical bonding material.

The cone may have extensions to provide for additional fixation of the cone to the lamina, spinous process, pedicle, and/or the transverse process. These extensions may be provided with holes for fixation to these structures by screws or the like. The extensions may also incorporate tabs or tongues that can be bent around the edge of the lamina, or around the transverse process.

The cone may be made of any conventional material usable for such spinal prostheses. Typically the cone is made of metal, e.g., cobalt-chromium-molybdenum alloy, stainless steel, titanium alloy, or other conventional alloy used for such prostheses, or of an appropriate synthetic polymer, or of a ceramic.

The cup-shaped prosthesis for the caudad vertebra ("the cup") has a hollow interior having a generally circular cross-section. The cross-sectional diameter of the cup is somewhat larger than that of the cone. Thus the cone is a rather loose fit within the cup. Furthermore, the interior surface of the cup wall has an angular flare that is somewhat greater than that of the cone, so that the angle between the outer wall of the cone and the inner wall of the cup is in a range of about 3° to about 10°. Accordingly, the cone fits loosely within the cup, and the mismatch of diameters and angles will allow for controlled lateral bending and rotation, with the cone sliding on the wall of the cup to provide support to replace the support provided by the natural facet joint.

When the spinal motion segment is in its neutral position, i.e., when the cephalad and caudad vertebrae are neither flexed, extended, laterally bent, or rotated with respect to one another, the end of the cone is positioned vertically somewhat above the bottom of the cup. The vertical position of the cone relative to the cup in the neutral position is selected so that upon full extension of the spinal motion segment, the tip of the cone is in contact with the bottom of the cup to provide a positive lock and a weight-bearing function.

As indicated above, the cup wall preferably has a generally circular cross section. However, it is not excluded that the cross section may deviate somewhat from an exact circle if necessary to provide proper function in a particular location in a particular patient. Furthermore, the cup wall may be cut away in some portions of its circumference in order to provide for certain functions and clearances. For example, the cup may have a lower rim, or a portion of the wall may be cut away at the anterior-medial portion of the cup in order to provide space for neural structures passing through that region, or to avoid impingement of the tip of the cone on the wall of the cup during flexion of the spinal motion segment.

Furthermore, the proximal-anterior end of the wall of the cup is preferably higher and flared outward along the contour of the anterior surface of the lamina of the pars interarticularis in order to provide guidance for the gliding of the cone during flexion.

The cup is typically provided with a base or other external extensions adapted for fixation of the cup to the superior articular process and/or adjacent bony structures of the caudad vertebra. Typically, the cup is fixed in position on the caudad vertebra by means of a pedicle screw passing through a hole in the base, etc., and into the pedicle and body of the vertebra. Preferably the screw is provided with an expandable sleeve that fits within the pedicle and is expanded by insertion of the pedicle screw to provide firm contact with the interior surface of an aperture made in the pedicle. Inasmuch as the pedicle has an oval-shaped cross-section, with a larger cranio-caudal diameter than right-left diameter, the expandable sleeve is also preferably has an oval cross-section in order to match the shape of the pedicle. Such an oval shape for the sleeve on the pedicle screw helps to prevent loosening of the screw by the imposition of repeated bending and/or torsional moments by motion of the spinal motion segments by the natural activities of the patient. Typically, expansion of the expandable sleeve is produced by providing two or more spreadable fingers extending from a body of the sleeve toward the interior of the vertebra. A central tapered bore, which may be threaded, extends from the outer end of the sleeve to the internal end, with the diameter of the bore being smaller at the internal end. In this way the internal ends of the fingers are expanded as the screw is inserted and press against the internal surface of the bony structure of the pedicle. The outer surface of the screw sleeve is preferably provided with a porous structure, e.g., by a coating of a porous material, for bone ingrowth.

The base may also be provided with at least a pair of ears or tabs projecting superiorly and inferiorly from the base of the cup near the pedicle screw hole. These ears may be bent around the base of the transverse process to provide additional strength and security to the fixation of the cup.

In addition to the mechanical fixation between the cup and the bone, bone cement such as poly(methyl methacrylate) (PMMA) bone cement or other chemical bonding materials may be used.

Preferably the anterior edge of the wall of the cup also has an extension (higher wall) that is slightly curved anteriorly and provides guidance to the cone during flexion of the spinal motion segment.

Typically the cup component of the facet joint prosthesis is made of metal, e.g., the same metals as the cone, as indicated above, or of a synthetic polymer, such as ultra high density polyethylene, or of a ceramic material.

The design of the facet joint prosthesis, as described above, will provide a wide range of variable contact surface area, weight transmission, freedom/restriction of motion stability and weight bearing, in order to reproduce, as closely as possible, the function and motion of the natural face joint. The amount of lateral bending and rotation of the spinal motion segment is controlled by the difference in diameter and flare angle, i.e., the "mismatch" or relatively loose fit, between the cone and cup as discussed above. Upon extension, i.e., when the patient assumes an extended posture for the spine, where the facet joints must provide more weight bearing and stability, there is a relatively tight fit between the cone and cup that provides more contact surface to provide such weight bearing and stability. During flexion, the cone fits more loosely in the cup, i.e., the "mismatch" increases, which allows more freedom of rotation and a lesser amount of weight bearing, while still providing continuous stabilization against shear, just as the natural facet joints provide such a function for the natural intervertebral disc. Even in the fully flexed position, the cone is still within the cup and provides stability and protection of the disc against any extreme rotation or bending.

The facet joint prosthesis of the invention is implanted and oriented at such an angle in the spinal motion segment as to provide support and guidance as close to the natural performance of the face joint as possible. Ordinarily the long axis of the cone and cup assembly is oriented in a range of from about 10° to about 30°, preferably about 15° to about 25°, and more preferably about 20°, medio-lateral on the coronal plane, and in a range of from about 10° to about 30°, preferably about 15° to about 25°, and more preferably about 20°, superior-inferior on the sagittal plane. Furthermore, the facet joint replacement by be unilateral or bilateral.

It will be recognized by those skilled in the art that certain variations can be made in the construction and implantation of the facet joint prosthesis of the invention. For example, the base of the cup component may have varying configurations at the contact are with the bone, depending on the size and shape of the remaining superior articular process after resection. Thus, the base of the cup component may have a conical recess, for implantation on a generally conical residual process, a shallow dome-shaped recess, for a more aggressively resected process, or even a flat or somewhat convex protruding surface for the case wherein substantially all of the superior articular process is resected.

In summary, the facet joint prosthesis of the invention exhibits the following properties and advantages with respect to prior known prosthesies.the a.) The prosthesis is capable of bearing weight by reason of the contact between the external surface of the cone and the internal surface of the cup when the spinal motion segment is in its neutral position. Furthermore, the prosthesis is capable of providing a positive lock at the fully extended position of the spinal motion segment.

b.) Stability, support, and control is provided throughout a range of motion that is typically greater than that provided by known devices, and is more effective throughout that range of motion (ROM). In particular:

Sliding contact between the external surface of the cone and internal surface of the cup provides shear stability throughout the range of flexion and extension of the spinal motion segment.

On full extension of the spinal motion segment, the prosthesis provides a positive limit for weight bearing and stability.

The prosthesis allows ample range of motion in flexion and extension, and may be superior in this respect to prior art device.

A range of motion in rotation is allowed and controlled by the "mismatch" between the diameters of the cone and the cup, but is limited, for stability, by the amount of the "mismatch".

The cone-cup combination provides for free, but controlled motion in rotation during flexion to an adequate degree, and is designed to exceed the rotational ROM provided by known facet joint prostheses.

A range of motion for side-bending is also provided and controlled by the "mismatch' between the diameters of the cone and cup.

c.) The spinal motion segment is stabilized by continuous but variable amount of contact between the surface area of the cone and that of the cup during the range of motion. In particular, stability is provided by the positive stop and lock between the cone and cup that provides weight-bearing function on full extension. Positive resistance against shear stress on the intervertebral disc is provided by the angle and orientation of the cone and cup throughout the flexionj-extension range of motion.

Certain preparation of the implantation sites of both the cone and cup is accomplished as follows, as described for a preferred embodiment of the prosthesis.

The inferior articular process is trimmed to receive the cone prosthesis. The inferior articular process of the facet joints in the lumbar spine is an extension of the lamina and has a characteristic triangular cross-sectional shape. In preparation for receiving the cone prosthesis, the inferior articular process is trimmed to form a triangular cross-sectional area to be fitted into the cone. A channel is drilled from the tip of the articular process in a cephalad direction to receive the axial projection within the central cavity of the cone. Such trimming provides decompression of the hypertrophic degenerative changes and provides positive mechanical locking between cone and bone against rotational and bending moments.

The superior articular process is the main structure causing spinal stenosis. Resection or trimming of the superior articular process provides thorough decompression of spinal stenosis and also provides the maximum surgical exposure window for any work on the disc space. The amount of resection/trimming may be varied depending on the amount of decompression required for relief of stenosis or exposure of the of the intervertebral disc or other structures. Representative amounts of trimming are as follows:

The facet of the superior articular process may be trimmed, leaving a generally cone-shaped bony protrusion that accepts a corresponding generally conical recess in the base of the cup component.

The superior one-third to one-half of the superior articular process may be resected, leaving a shallow dome to accept a corresponding shallow recess in the base of the cup component.

The entire superior articular process may be resected, leaving exposed the pedicle to which the base of the cup component is fixed.

The invention will now be illustrated with reference to the drawings, which illustrate certain preferred embodiments of the invention.

Figure 2:
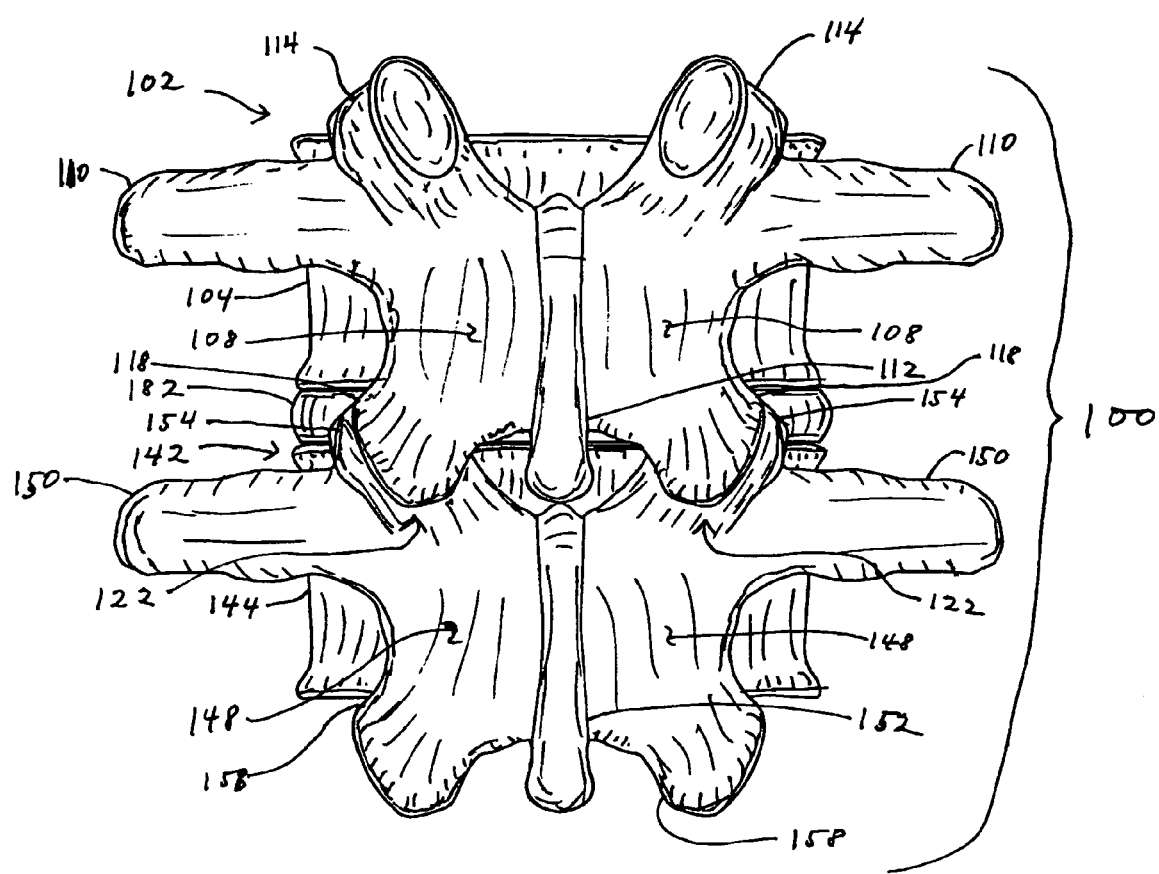
FIG. 2 shows a dorsal view of the spinal motion segment.

FIGS. 1 and 2 show, respectively, a schematic lateral view of a region of the lumbar spine and a dorsal view of the same region wherein a particular spinal motion segment 100 is designated. The spinal motion segment 100 comprises a cephalad vertebra 102 and a caudad vertebra 142. The cephalad vertebra 102 includes a vertebral body 104, pedicles 106, laminae 108, transverse processes 110, a spinous process 112, superior articular processes 114, having facets 116, and inferior articular processes 118. The caudad vertebra 142 includes a vertebral body 144, pedicles 146, laminae 148, transverse processes 150, a spinous process 152, superior articular processes 154, having facets 156, and inferior articular processes 158. An intervertebral disc 182 separates the cephalad vertebra 102 and the caudad vertebra 142.

Figure 3:
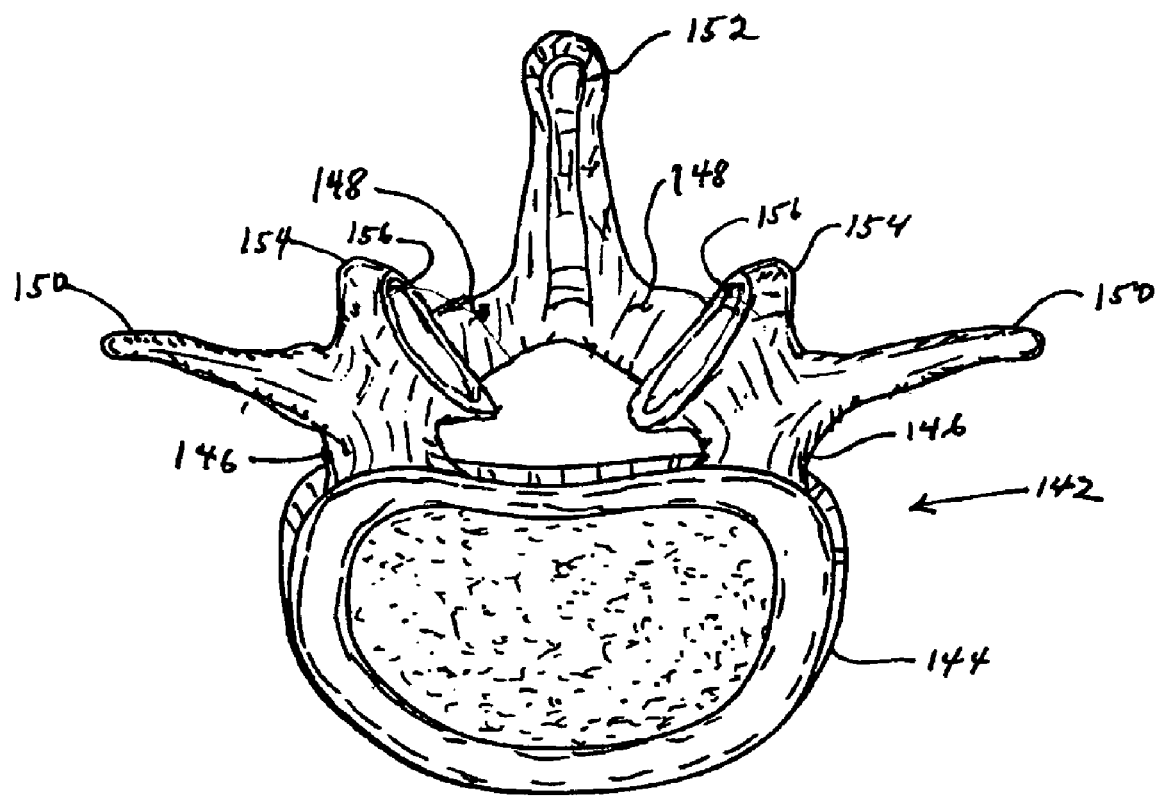
FIG. 3 shows a view of a lumbar vertebra from the cranial aspect.

FIG. 3 shows the lower lumbar vertebra 142 of the spinal motion segment 100 from a cranial aspect.

Figure 4:
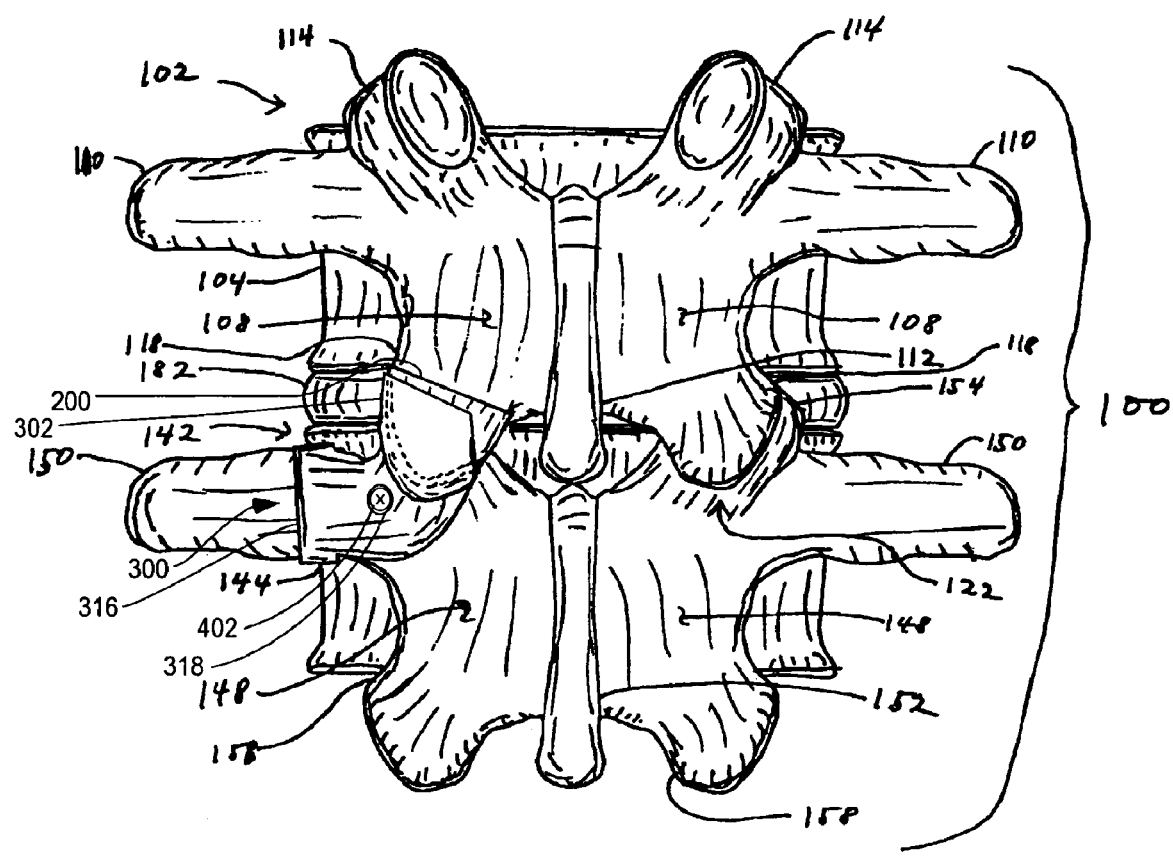
FIG. 4 is a dorsal view of the spinal motion segment with a facet joint prosthesis of the invention implanted therein.
Figure 5:
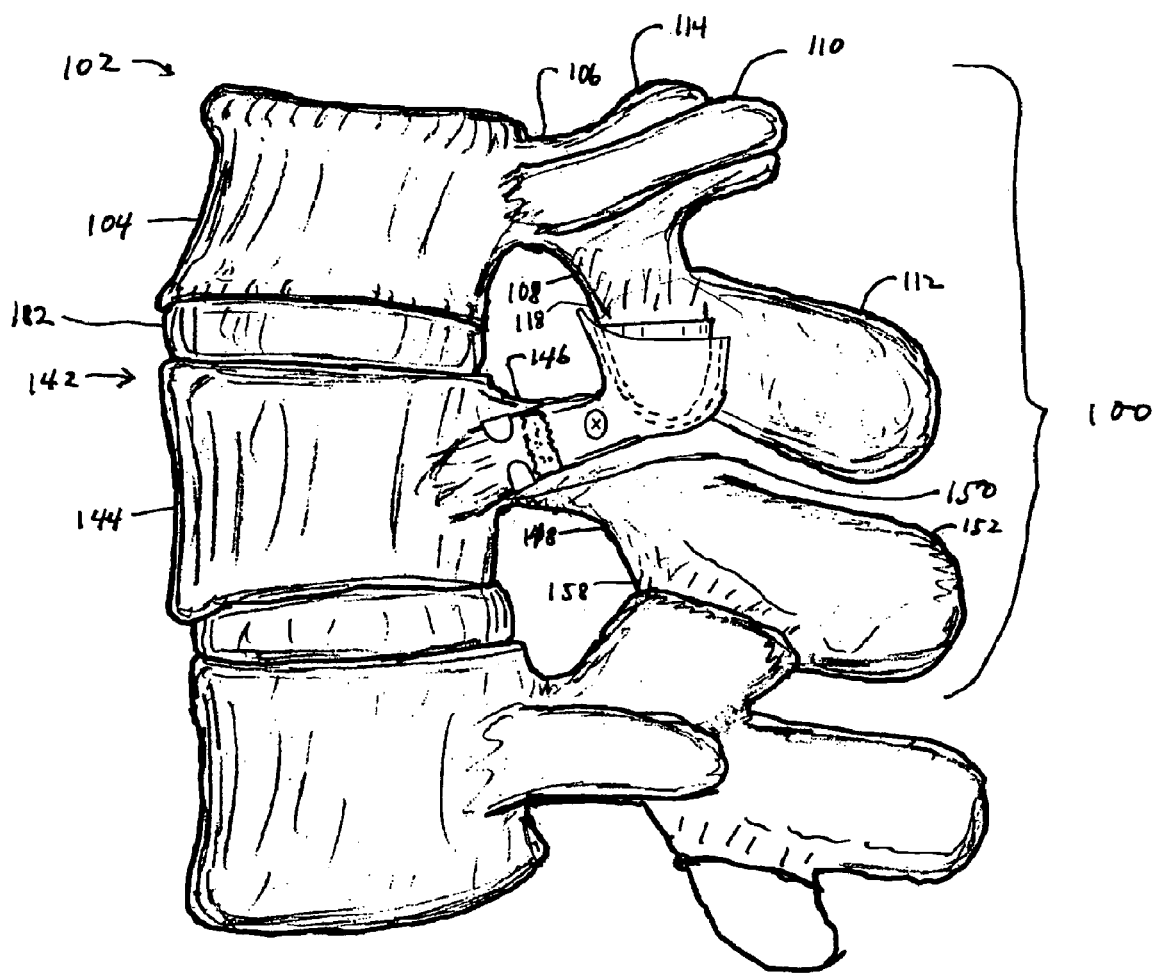
FIG. 5 is a lateral view of the spinal motion segment with a facet joint prosthesis of the invention implanted therein.
Figure 6:
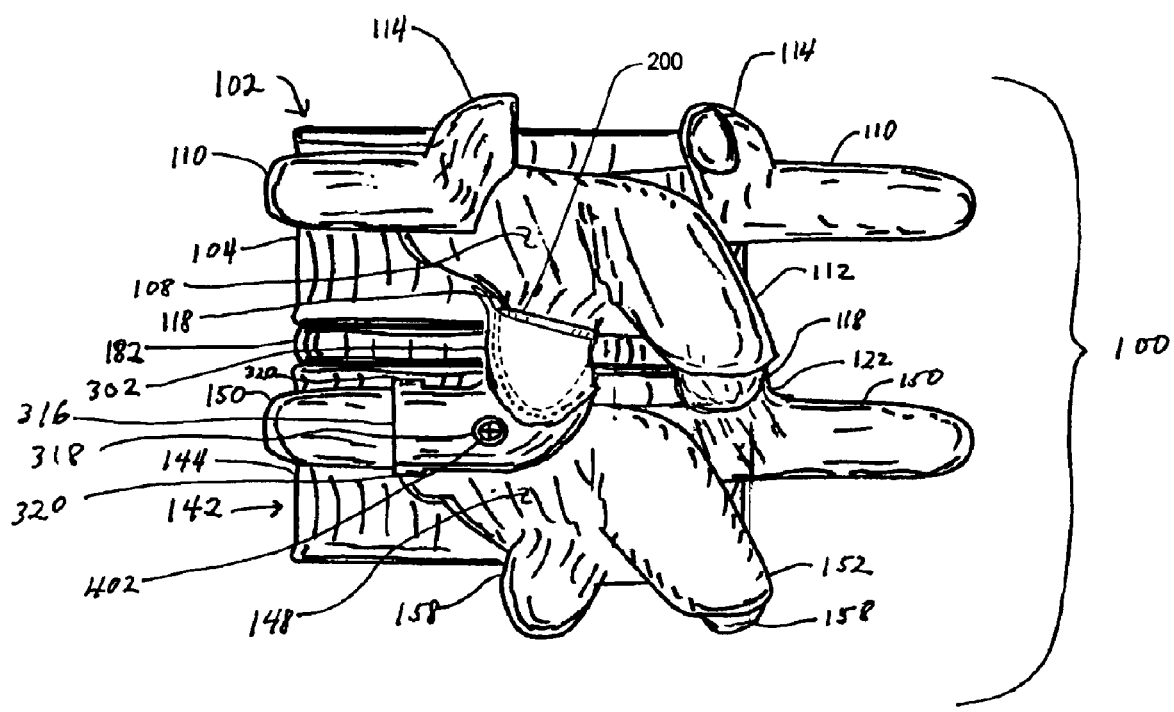
FIG. 6 is a dorso-lateral angular view of the spinal motion segment with a facet joint prosthesis of the invention implanted therein.

FIGS. 4 and 5 are, respectively, a dorsal view and a lateral view of the spinal motion segment 100 with the facet joint prosthesis of the invention implanted therein. FIG. 6 presents an oblique left latero-dorsal view of the spinal motion segment with the prosthesis implanted therein.

Figure 9A:
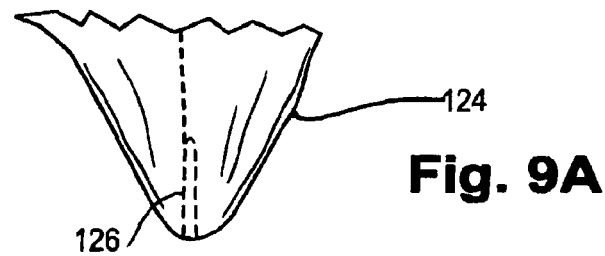
FIG. 9A shows the tip of a lower articular process, as resected for implantation of the cone element of the fact joint prosthesis, having a generally triangular configuration.
Figure 9B:
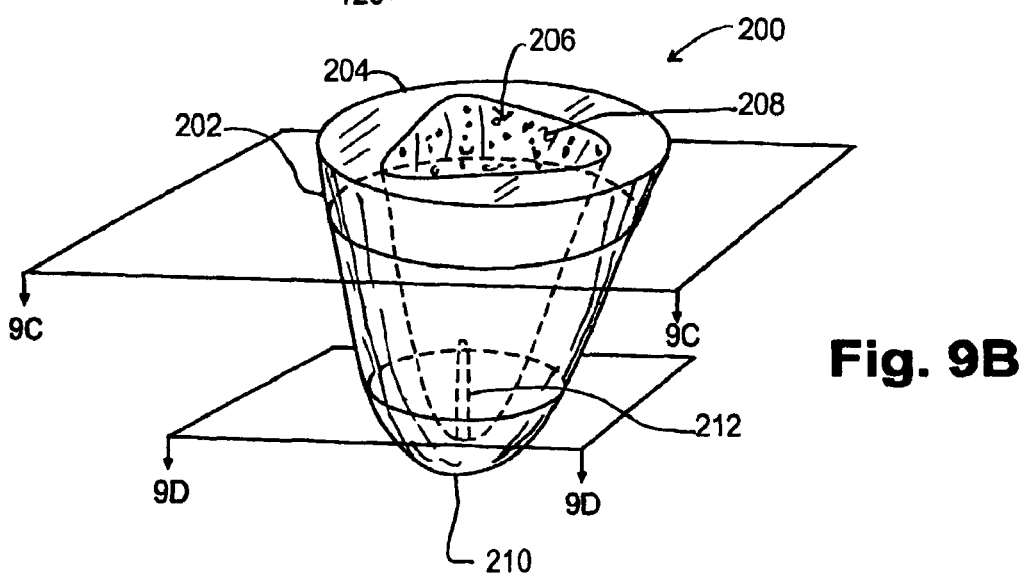
FIG. 9B shows a preferred embodiment of the conical prosthesis adapted for implantation on a surgically prepared site on the distal end of an inferior articular process.
Figure 9C:
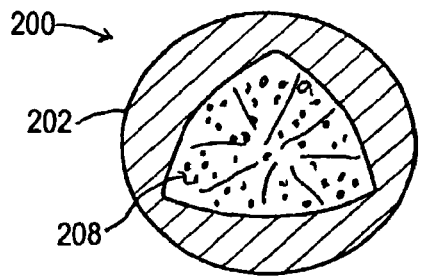
FIGS. 9C and 9D show cross-sections of the prosthesis of FIG. 9B taken at the planes indicated as 9C-9C and 9D-9D, respectively, in FIG. 9B.
Figure 9D:
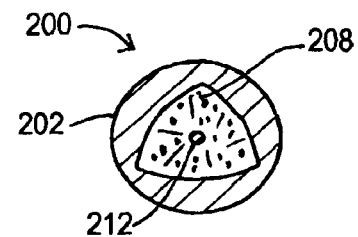

In these figures, the cone component 200 is fixed to the appropriately trimmed inferior articular process 118 of the cephalad vertebra 102. A detail view of the trimmed tip 124 of the inferior articular process 118 with internal channel 126 for receiving a corresponding projection on the cone may be seen in FIG. 9A.

FIGS. 9A-9D illustrate a preferred embodiment of the cone component 200. The cone 200 has an upper rim 204 and a tip 210, with an external surface 202 that is generally smooth and adapted to glide on the internal surface of the cup. The cone 200 has an internal cavity 206 that has a generally triangular cross-section in the illustrated embodiment. The internal surface 208 of the cavity 206 is preferably porous in order to promote bone ingrowth. Such a porous surface 208 may be provided by any conventional technique such as a porous coating, texturing or etching the surface, or other conventional procedure used to produce a porous ingrowth-promoting surface on bone implants in suitable for preparing a porous surface for implants used in orthopedic surgery. In the illustrated preferred embodiment, the cone 200 is also provided with an internal projection 208 extending axially from the inner surface 208 at the tip 210 of the cone 200.

Figure 10:
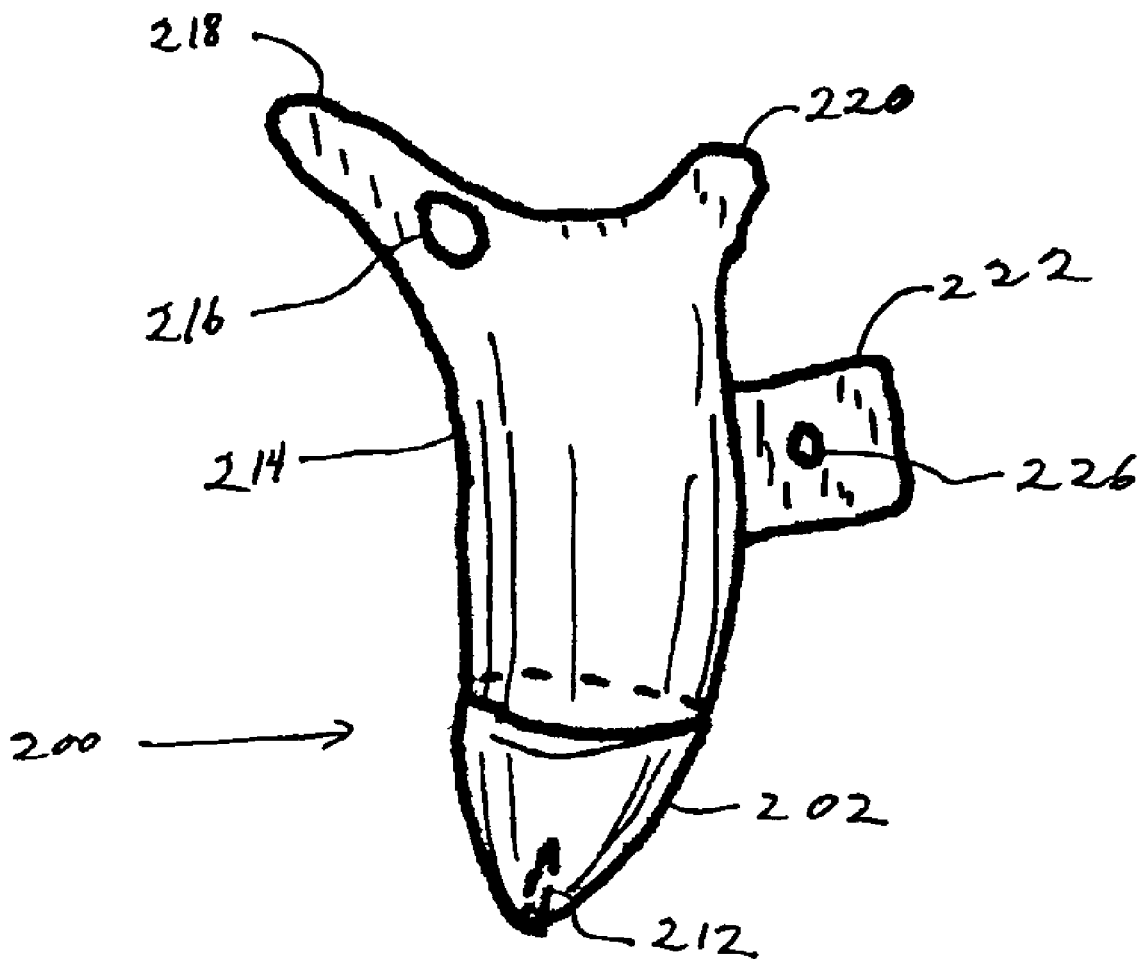
FIG. 10 illustrates an alternate embodiment of the conical superior element of the prosthesis of the invention.
Figure 11:
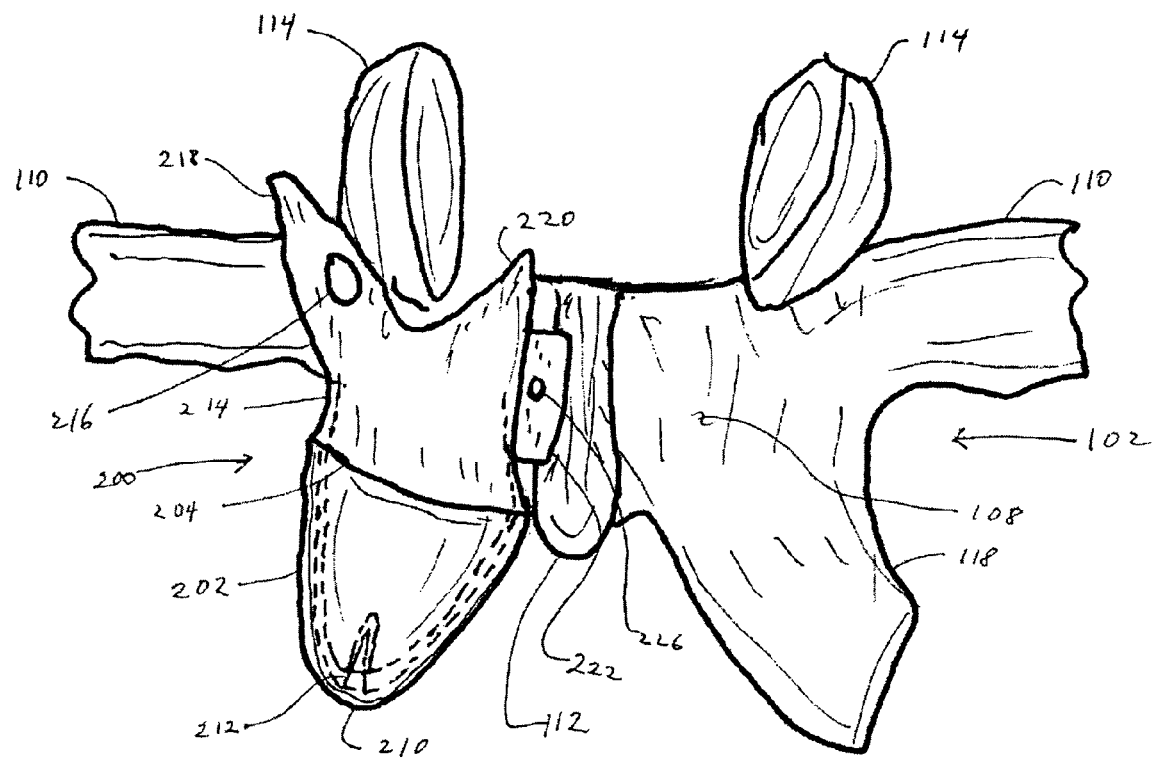
FIG. 11 shows the conical superior element of FIG. 10 implanted on the inferior articular process of a vertebra

An alternate embodiment of the cone prosthesis is illustrated in FIG. 10, and a schematic detail of such a prosthesis implanted on an inferior articular process of a cephalad vertebra is shown in FIG. 11. This embodiment of the cone 200 incorporates an extension 214 extending upward from the rim 204 and provided with a hole 216 for a bone screw. The extension 214 also has tabs 218 and 220 adapted to be bent over adjacent anatomical structures such as the lamina and transverse process. The extension 214 is also provided with a side tab 222 adapted to contact the adjacent surface of the spinous process, and the side tab 222 is also provided with a hole 226 for a bone screw to fix it to the spinous process.

FIGS. 8A-8E illustrate a preferred embodiment of the cup component of the facet joint prosthesis. The cup component 300 of the facet joint prosthesis is fixed to the caudad vertebra 142 at the general location of the superior articular process 154, which is appropriately resected. The cup component 300 comprises a cup 302, having a wall 304 with a rim 306. The interior surface 308 of the cup wall 304 is smooth to provide a surface upon which the exterior surface 202 of the cup 200 may glide easily and smoothly. A cut-out portion 310 is formed in the anterior-medial section of the wall to limit restriction of the vertebral canal by the cup prosthesis. The anterior-lateral portion of the wall of the cup has an extension 314 that extends upward and is flared outward. This extension 314 provides a surface upon which the cone may glide, particularly in flexion of the spinal motion segment 100. The cup 302 is provided with a base or mounting extension 316 extending from the lower portion of the cup wall 304 generally in a lateral direction for contact with the adjacent bony structures, e.g., the lamina, the pedicle and the transverse process. The base 316 is fixed to the vertebra by a pedicle screw through hole 318 therein. The base 316 is also preferably provided with tabs 320 positioned to be bent around the base of the transverse process to further fix the cup component 300 in position, as shown in FIG. 5 (wherein the distal portion of the transverse process has been deleted to provide a clearer visualization of the implant).

Figure 7:
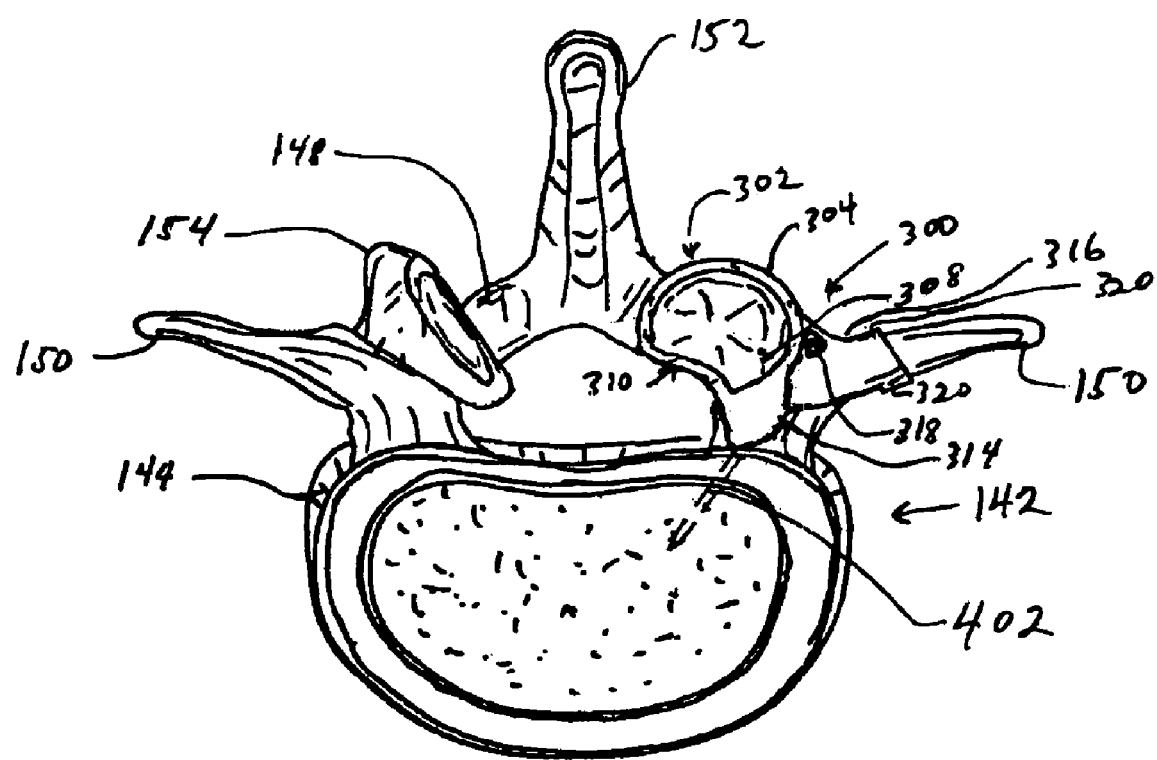
FIG. 7 is a cranial view of a lumbar vertebra with the superior articular process prosthesis of the invention implanted therein.

FIG. 7 shows a cranial aspect view of the cup prosthesis implanted in the lower lumbar vertebra of FIG. 3, and fixed therein by pedicle screw assembly 400 (shown in phantom).

The pedicle screw assembly 400 is illustrated in FIGS. 12A-12F. The pedicle screw assembly 400 comprises a pedicle screw 402, of generally conventional design, and a sleeve 404, designed to fit within a cavity prepared in the pedicle and to expand against the inner surface of the cavity to provide a stronger fixation than that provided by a pedicle screw alone. The sleeve 404 has a generally oval cross-section to conform generally to the oval cross section of the pedicle. The outer end 406 of the sleeve is solid, while the internal end 408 is provided with a number of slits 410 extending from the inner end 408 toward the outer end. The slits 410 thereby create a number of fingers 412 extending from the outer end toward the inner end. The sleeve 402 is provided with a tapered bore 414 extending from the outer end 406 to the inner end 408. When the sleeve is in its initial form, the fingers 412 extend generally parallel, and are not expanded, as shown in FIG. 12A and cross-sections 12B and 12C. The sleeve 400 is inserted in this initial form into a cavity formed in the pedicle. The cup component of the facet joint prosthesis is then placed in position and the pedicle screw is inserted through the hole 318 in the cup base 316 and advanced through the tapered internal bore 414 of sleeve 400 and into the pedicle of the vertebra. Thereby, the fingers 412 of the sleeve 404 are expanded, as shown in FIGS. 12E and 12F, and press against the walls of the cavity formed in the pedicle. Preferably the outer surface 416 of the sleeve 404 is provided with a porous structure, as is conventional in the orthopedic surgery art. Such porous structures may be produced by conventional treatments or coatings. The pedicle screw and sleeve may be made of conventional alloys used in orthopedic surgery, such as stainless steel, titanium alloys, or the like.

Figure 13A:
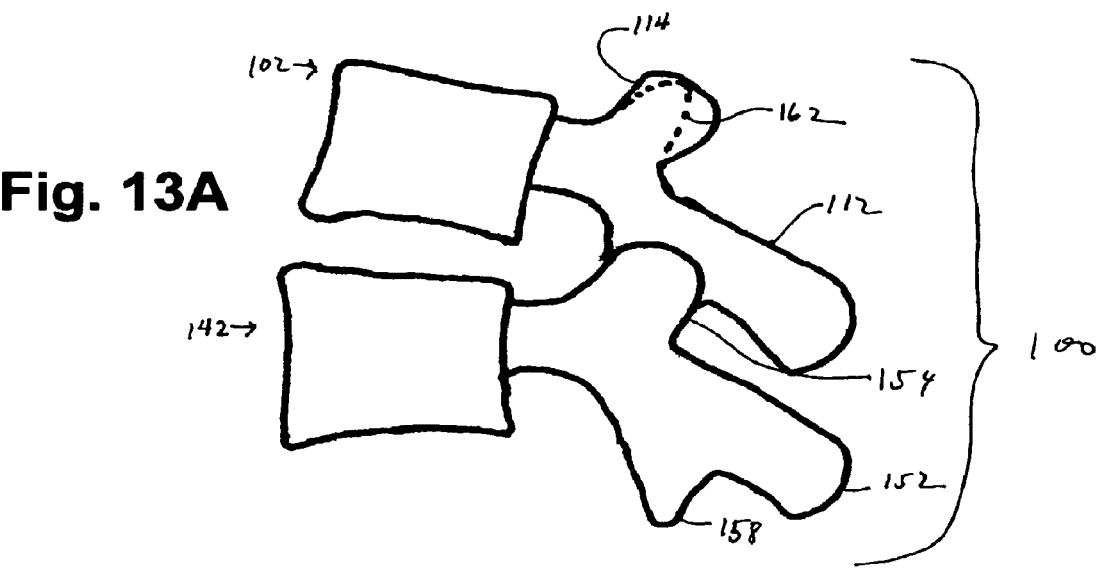
FIGS. 13A, 13B And 13C show schematic lateral views of a spinal motion segment indicating different amounts of the superior articular prosthesis that can be resected in order to provide a site for implantation of the inferior cup-shaped element of the prosthesis of the invention.
Figure 13B:
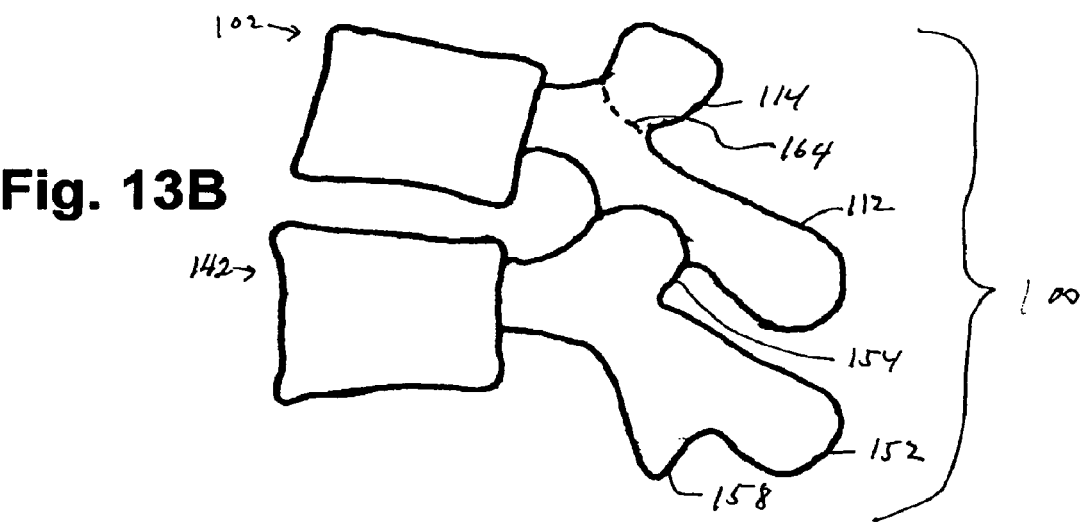
Figure 13C:
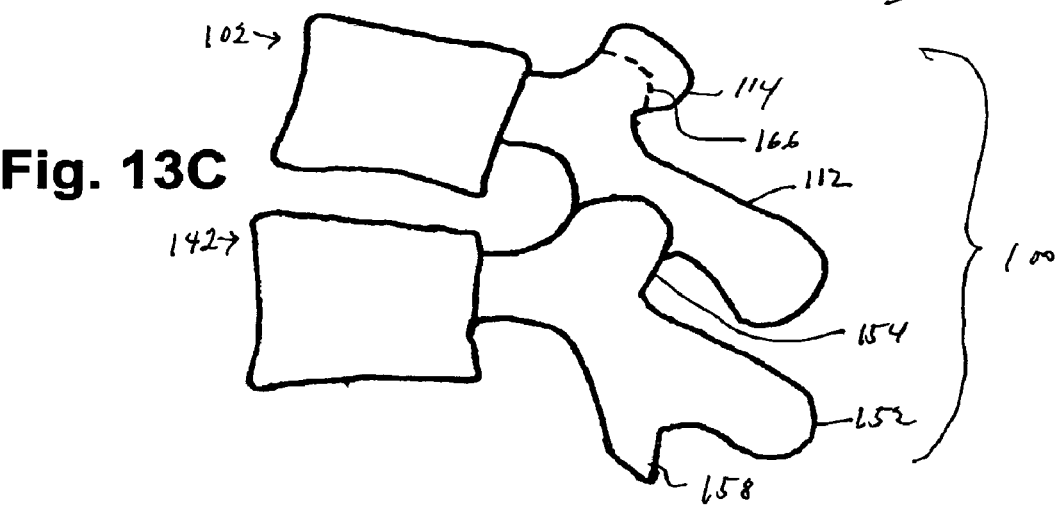

In order to provide an appropriate site for implantation of the cup component 300, the superior articular process 154 of the caudad vertebra 142 is resected. Various possibilities for such resection are indicated in FIGS. 13A-13C by dashed lines. FIG. 13A indicates a resection leaving a generally conical site 162. FIG. 13B indicates an extensive resection leaving a shallow or flat depression 164. FIG. 13C indicates a resection leaving a flat or shallow dome-shaped projection 166. The embodiments of the cup 300 that are intended for implantation at the sites illustrated in FIGS. 13A-13C are illustrated in FIGS. 14A-14, respectively.

The invention having been described above in terms of certain embodiments, it will be apparent to those skilled in the art that many changes and alterations can be made without departing from the spirit or essential characteristics of the invention. All embodiments incorporating such changes are intended to be included within the invention. The present disclosure is therefore to be considered as illustrative and not restrictive, the scope of the invention being indicated by the appended claims, and all changes which come within the meaning and range of equivalency are intended to be included therein.

I claim:

1. A prosthetic implant for replacing a facet joint in a spinal motion segment of a human spinal column comprising:
a superior component adapted to be implanted at a surgically prepared site on an inferior articular process of a cephalad vertebra of said spinal motion segment, said superior component comprising a generally conical prosthesis having a smooth generally conical external surface and a tapered internal cavity adapted to be implanted on a tapered resected portion of said inferior articular process of said cephalad vertebra, and
an inferior component adapted to be implanted at a surgically prepared site on a superior articular process of a caudad vertebra of the spinal motion segment, said inferior component comprising a cup having a sidewall and a hollow interior, and a base adapted to be implanted at said surgically prepared site on said superior articular process with said cup being oriented cephalad to receive said external surface of said superior component within said hollow interior,
said sidewall of said cup having an inner surface configured with a flare such that upon full extension of said spinal motion segment said generally conical prosthesis fits tightly within said sidewall of said cup and upon flexion of said spinal motion segment, said generally conical prosthesis fits loosely within said sidewall of said cup.

2. The prosthetic implant of claim 1, wherein said tapered internal cavity of said generally conical prosthesis has a generally triangular cross-section.

3. The prosthetic implant of claim 1, wherein said tapered internal cavity of said generally conical prosthesis is provided with a porous surface.

4. The prosthetic implant of claim 1, wherein said generally conical prosthesis has a radiused tip.

5. The prosthetic implant of claim 1, wherein said generally conical prosthesis is provided with at least one extension for affixing said generally conical prosthesis to said inferior articular process.

6. The prosthetic implant of claim 5, wherein said extension is provided with a hole for a bone screw.

7. The prosthetic implant of claim 5, wherein said extension is provided with at least one tab for bending around at least a portion of said inferior articular process.

8. The prosthetic implant of claim 1, wherein said cup of said inferior component has a smooth internal surface.

9. The prosthetic implant of claim 1, wherein a portion of said sidewall of said cup of said inferior component is removed at a medial-anterior position thereof.

10. The prosthetic implant of claim 1, wherein said sidewall of said cup extends upward and outward at an anterior position thereof.

11. The prosthetic implant of claim 1, wherein said base of said inferior component is provided with a hole for a pedicle screw.

12. The prosthetic implant of claim 1, wherein said base of said inferior component is provided with tabs adapted to be bent around an adjacent anatomical structure.

13. The prosthetic implant of claim 12, wherein said tabs are adapted to be bent around at least a portion of a transverse process of said caudad vertebra.

14. The prosthetic implant of claim 1, wherein said base of said inferior component is adapted to be implanted at a site on said superior articular process resected to provide a generally conical site.

15. The prosthetic implant of claim 1, wherein said base of said inferior component is adapted to be implanted at a site on said superior articular process resected to provide a generally flat site.

16. The prosthetic implant of claim 1, wherein said base of said inferior component is adapted to be implanted at a site on said superior articular process resected to provide a generally dome-shaped site.

17. A method of replacing a degenerated facet joint in a spinal motion segment of a human spinal column, said method comprising:
providing a prosthetic implant including:
a superior component adapted to be implanted at a surgically prepared site on an inferior articular process of a cephalad vertebra of said spinal motion segment, said superior component comprising a generally conical prosthesis having a smooth generally conical external surface and a tapered internal cavity adapted to be implanted on a tapered resected portion of said inferior articular process of said cephalad vertebra, and
an inferior component adapted to be implanted at a surgically prepared site on a superior articular process of a caudad vertebra of the spinal motion segment, said inferior component comprising a cup having a sidewall and a hollow interior, and a base adapted to be implanted at said surgically prepared site on said superior articular process with said cup being oriented cephalad to receive said external surface of said superior component within said hollow interior,
said sidewall of said cup having an inner surface configured with a flare such that upon full extension of said spinal motion segment said generally conical prosthesis fits tightly within said sidewall of said cup and upon flexion of said spinal motion segment, said generally conical prosthesis fits loosely within said sidewall of said cup; and
removing at least a portion of the degenerated facet joint, to form the respective surgically prepared sites on the caphalad vertebra and the caudad vertebra of the spinal motion segment, and replacing the removed portion with said prosthetic implant.

18. A prosthetic implant for replacing a facet joint in a spinal motion segment of a human spinal column comprising:
a superior component adapted to be implanted at a surgically prepared site on an inferior articular process of a cephalad vertebra of said spinal motion segment, said superior component comprising a generally conical prosthesis having a smooth generally conical external surface and a tapered internal cavity adapted to be implanted on a tapered resected portion of said inferior articular process of said cephalad vertebra, and
an inferior component adapted to be implanted at a surgically prepared site on a superior articular process of a caudad vertebra of the spinal motion segment, said inferior component comprising a cup, having a sidewall and a hollow interior, and an attachment portion adapted to be implanted at said surgically prepared site on said superior articular process with said cup being oriented cephalad to receive said external surface of said superior component within said hollow interior,
said sidewall of said cup having an inner surface configured with a flare such that upon full extension of said spinal motion segment said generally conical prosthesis fits tightly within said sidewall of said cup and upon flexion of said spinal motion segment, said generally conical prosthesis fits loosely within said sidewall of said cup.

19. The prosthetic implant of claim 18, wherein said attachment portion of said inferior component is provided with a hole for a pedicle screw.

20. The prosthetic implant of claim 18, wherein said attachment portion of said inferior component is provided with tabs adapted to be bent around an adjacent anatomical structure.

21. The prosthetic implant of claim 20, wherein said tabs are adapted to be bent around at least a portion of a transverse process of said caudad vertebra.

22. A method of replacing a degenerated facet joint in a spinal motion segment of a human spinal column, said method comprising:

provoiding a prosthetic implant including:

a superior component adapted to be implanted at a surgically prepared site on an inferior articular process of a cephalad vertebra of said spinal motion segment, said superior component comprising a generally conical prosthesis having a smooth generally conical external surface and a tapered internal cavity adapted to be implanted on a tapered resected portion of said inferior articular process of said cephalad vertebra, and an inferior component adapted to be implanted at a surgically prepared site on a superior articular process of a caudad vertebra of the spinal motion segment, said inferior component comprising a cup having a sidewall and a hollow interior, and an attachment portion to be implanted at said surgically prepared site on said superior articular process with said cup being oriented cephalad to receive said external surface of said superior component within said hollow interior, said sidewall of said cup having an inner surface configured with a flare such that upon full extension of said spinal motion segment said generally conical prosthesis fits tightly within said sidewall of said cup and upon flexion of said spinal motion segment, said generally conical prosthesis fits loosely within said sidewall of said cup; and removing at least a portion of the degenerated facet joint, to form the respective surgically prepared sites on the caphalad vertebra and the caudad vertebra of the spinal motion segment, and replacing the removed portion with said prosthetic implant.

\* \* \* \* \*